United States Patent
Kunimune et al.

(10) Patent No.: US 6,776,059 B2
(45) Date of Patent: Aug. 17, 2004

(54) METHOD AND DEVICE FOR SAMPLING AND STORING URINE SPECIMEN

(76) Inventors: Noriaki Kunimune, c/o Kunimune Co., Ltd., 14-8, Takaida, Higashiosaka-shi, Osaka 577-0053 (JP); Shinichi Yokoyama, c/o Kunimune Co., Ltd., 14-8, Takaida, Higashiosaka-shi, Osaka 577-0053 (JP); Shigeaki Baba, c/o International Institute for Diabetes Education & Study, Tokiwa Bldg. 7F, 30, Akashi-cho, Chuo-ku, Kobe-shi, Hyogo 650-0037 (JP); Yasuro Kameno, c/o International Institute for Diabetes Education & Study, Tokiwa Bldg. 7F, 30, Akashi-cho, Chuo-ku, Kobe-shi, Hyogo 650-0037 (JP)

( * ) Notice: Subject to any disclaimer, the term of this patent is extended or adjusted under 35 U.S.C. 154(b) by 0 days.

(21) Appl. No.: 10/344,082

(22) PCT Filed: Jul. 12, 2001

(86) PCT No.: PCT/JP01/06056

§ 371 (c)(1), (2), (4) Date: Feb. 6, 2003

(87) PCT Pub. No.: WO02/14832

PCT Pub. Date: Feb. 21, 2002

(65) Prior Publication Data

US 2003/0164051 A1 Sep. 4, 2003

(30) Foreign Application Priority Data

Aug. 11, 2000  (JP) ........................................ 2000-244555

(51) Int. Cl.$^7$ .............................................. G01N 1/00
(52) U.S. Cl. .................................. 73/864.52; 73/863.23
(58) Field of Search ......................... 73/864.52, 864.73, 73/864.74, 863.23

(56) References Cited

U.S. PATENT DOCUMENTS

| 4,300,404 | A | | 11/1981 | Mehl et al. |
| 4,812,293 | A | * | 3/1989 | McLaurin et al. ............. 422/69 |
| 5,137,031 | A | * | 8/1992 | Guirguis ..................... 128/771 |
| 5,714,696 | A | * | 2/1998 | Yeamans .................. 73/863.84 |
| 6,145,688 | A | * | 11/2000 | Smith ......................... 220/259 |

FOREIGN PATENT DOCUMENTS

| EP | 0321064 A1 | 1/1988 | ........... B01D/23/28 |
| JP | 63-140935 | 6/1988 | ............. G01N/1/00 |
| JP | 9-5322 | 1/1997 | .......... G01N/33/50 |
| JP | 9-196909 | 7/1997 | .......... G01N/33/48 |
| JP | 2001-108581 | 4/2001 | ............ G01N/1/10 |
| WO | WO96/39923 A1 | 12/1996 | ............ A61B/5/00 |

* cited by examiner

*Primary Examiner*—Robert Raevis
(74) *Attorney, Agent, or Firm*—Darby & Darby (57) ABSTRACT

A method and a device for sampling and storing a urine specimen capable of recovering a sampled urine specimen to a recovery container (5) through a filter (2) by the sucking pressure of the decompressed and enclosed recovery container (5); the device for sampling and storing the urine specimen, comprising a filter holder (3) having a space for storing the filter (2) for filtrating the urine specimen, the filter (2) stored therein, and the recovery container (5) decompressed and enclosed by a plug body (4), wherein hollow tubes (6) with a sharp tip communicating with a space (S) having the filter (2) stored therein is installed in the filter holder (3) on a specimen delivery side to the recovery container (5).

12 Claims, 8 Drawing Sheets

METHOD AND DEVICE FOR SAMPLING AND STORING URINE SPECIMEN

This is a U.S. national phase application under 35 U.S.C. §371 of International Patent Application No. PCT/JP01/06056, filed Jul. 12, 2001, and claims the benefit of Japanese Patent Application No. 2000-244555, filed Aug. 11, 2000. The International Application was published in Japanese on Feb. 21, 2002 as WO 02/14832 A1 under PCT Article 21(2).

TECHNICAL FIELD

The present invention relates to a method and a device for enabling a long-time storage of a sampled urine specimen preventing change in its property for urinalysis in the field of clinical diagnosis.

BACKGROUND INFORMATION

Urinalysis is broadly conducted as a screening test in a first examination for outpatients and a group examination and as a common test in observation of progress because in which it is possible to examine patients without giving them a load at the moment of sampling a specimen.

Since urine specimens sampled from patients are changed by exogenous and endogenous germs, oxygen and light comparatively soon, they had better be tested within 3–4 hours after being sampled. When urine specimens are left untested for more than 3–4 hours after being sampled, they need to be hermetically kept in a refrigerator or a freezer. In a group examination where a large volume of urine specimens must be tested, specimens are usually kept refrigerated or frozen, and put back to their normal condition at the time of examination.

However, while being let to stand in ambient air, sampled specimens, in which germs could be propagated by exogenous and endogenous germs, could be changed in their constituents.

Furthermore, some constituents of urine specimens are so sensitive to oxygen and light that leaving them in ambient air could cause an inaccurate test.

Especially, when many specimens are tested in a group examination, an inefficient way have to be chosen; for example, samplers and testing devices have to be continuously at work for a prompt test, or urine specimens must be hermetically kept in a refrigerator or a freezer, and defrosted before a test.

Moreover, urine specimens sampled in regions and facilities where no testing equipment is available are inevitably required not only to be airtightly kept in a refrigerator or a freezer, but also to be sent in the same conditions to another facility for a test using uneconomical transportation.

It is therefore an object of the present invention to solve the conventional problems mentioned above and to provide a method and a device for sampling and storing a urine specimen, which allow accurate testing of sampled specimens preventing change in constituents even after a several-day storage at room temperature, and easy transportation of sampled specimens collected in a group examination without refrigeration or other treatment.

SUMMARY OF THE INVENTION

A method for sampling and storing a urine specimen according to the present invention includes filtering a sampled urine specimen through a filter, decompressing and sealing a recovery container, and recovering the sampled urine specimen into the recovery container using sucking pressure therein.

A device for sampling and storing a urine specimen according to the present invention includes a sampling cup, a filter for a urine specimen, a filter holder for holding the filter, a plug, a recovery container decompressed and sealed with the plug. The filter holder has a space to hold the filter inside and tubes with sharp tips respectively communicating with the space at both of its outlet and inlet sides for a specimen.

The filter holder, which has the space to hold the filter inside, may have a communicating hole communicating with a bottom hole of the sampling cup at its inlet side for a specimen and a tube with a sharp tip communicating with the space of the filter holder at its outlet side.

Furthermore, a device for sampling and storing a urine specimen according to the present invention includes a filter for a urine specimen, a filter holder receiving the filter, a plug, a recovery container decompressed and sealed with the plug. The filter holder is provided with a space for holding the filter, an outer cover extending upward on its outlet side for a specimen, a tube with a sharp tip communicating with the space within the outer cover, and a specimen suction tube communicating with the space on its inlet side of the specimen. The recovery container is insertable into the outer cover of the filter holder with the plug ahead.

In the device for sampling and storing a urine specimen according to the present invention, the filter holder favourably has a pore size of 0.05 $\mu$m–0.2 $\mu$m.

And also, in the device for sampling and storing a urine specimen according to the present invention, the recovery container does not favourably transmit light.

Furthermore, in the device for sampling and storing a urine specimen according to the present invention, the pressure in the recovery container is favourably 0.1 atm–0.5 atm, and the recovery container is favourably decompressed and sealed after being filled with inert gas.

The above-mentioned method and device allow removing germs from a sampled and stored urine specimen by filtering so as to prevent constituents from being changed by germ contamination and influence of oxygen and light, and a long-time storage without refrigeration or other treatment.

DESCRIPTION OF PREFERRED EMBODIMENTS

Embodiments according to the present invention are described in detail below in conjunction with the accompanying drawings.

Figure 1:
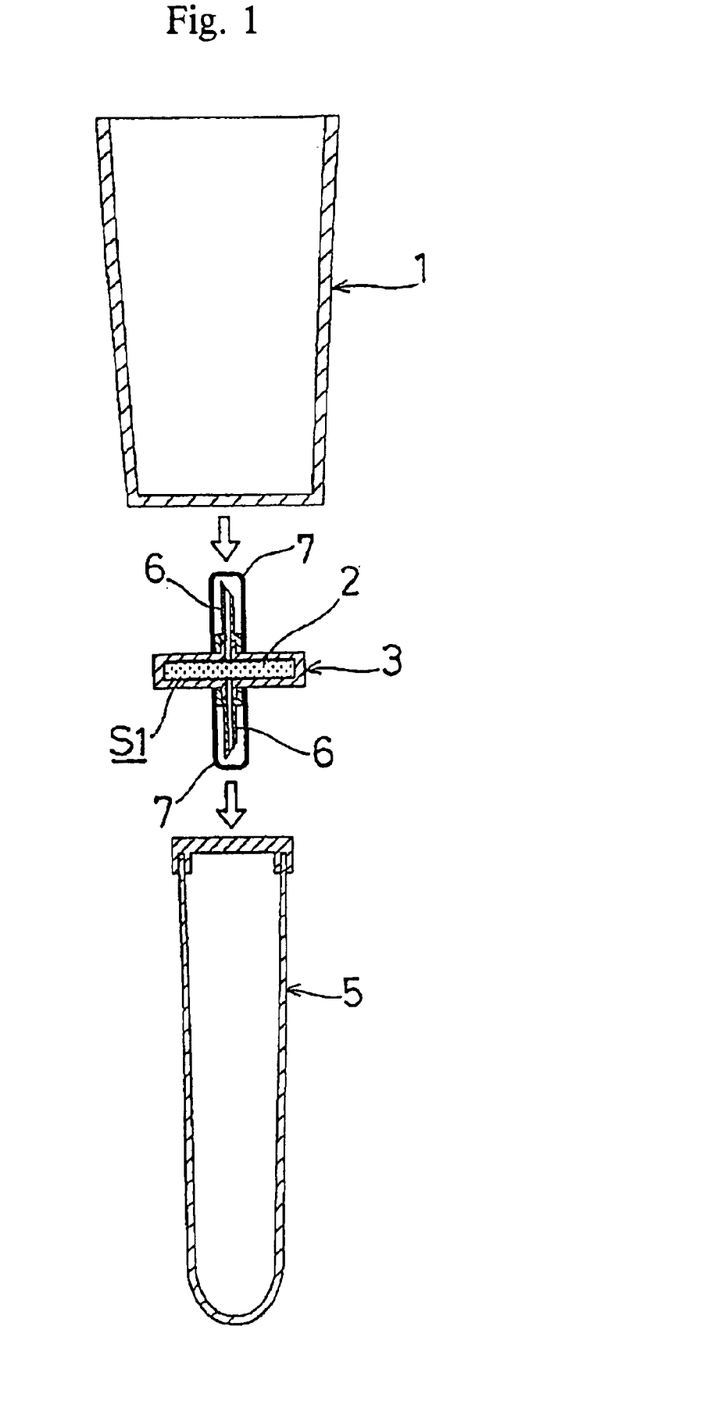
FIG. 1 is a sectional view of an embodiment of a device for sampling and storing a urine specimen according to the present invention.
Figure 3:
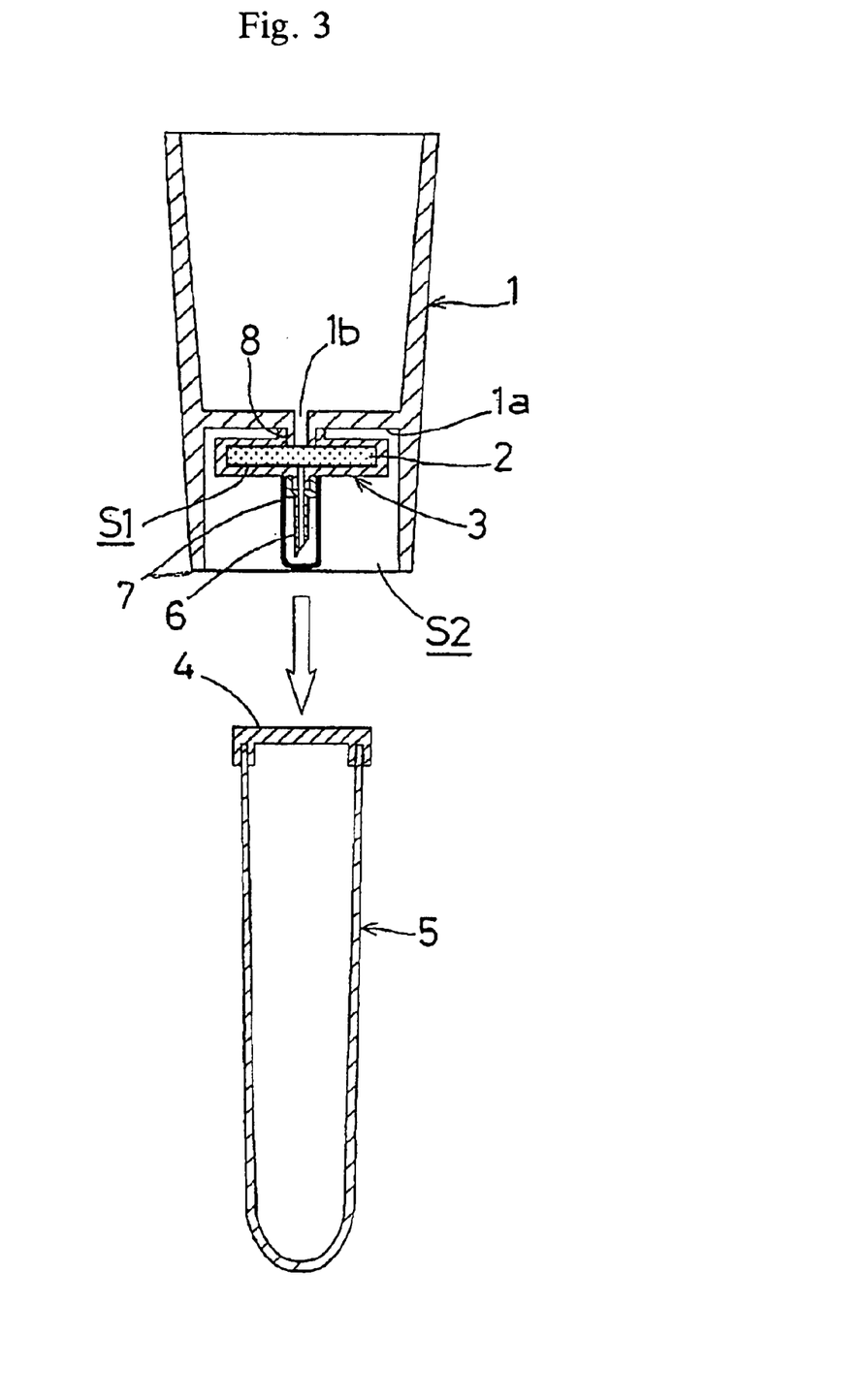
FIG. 3 is a sectional view of another embodiment of a device for sampling and storing a urine specimen according to the present invention.

A device for sampling and storing a urine specimen of the present invention, as shown in FIGS. 1 and 3, includes a sampling cup 1 to sample urine, a filter 2 for a urine specimen, a filter holder 3 holding the filter 2, a plug 4, and a recovery container 5 decompressed and sealed with the plug 4.

In FIG. 1, the filter holder 3 has a space S1 holding the filter 2 inside. The space S1 is provided with needles 6 respectively on an upper inlet and a lower outlet sides for a specimen, and the needles are in the form of a tube with a sharp tip and respectively communicating with the space S1. A thin rubber cap 7 covers around the needle 6 so as to prevent sampled urine from leaking out and/or avoid a user's injury such as pricking his or her fingers with the needle.

Figure 2:
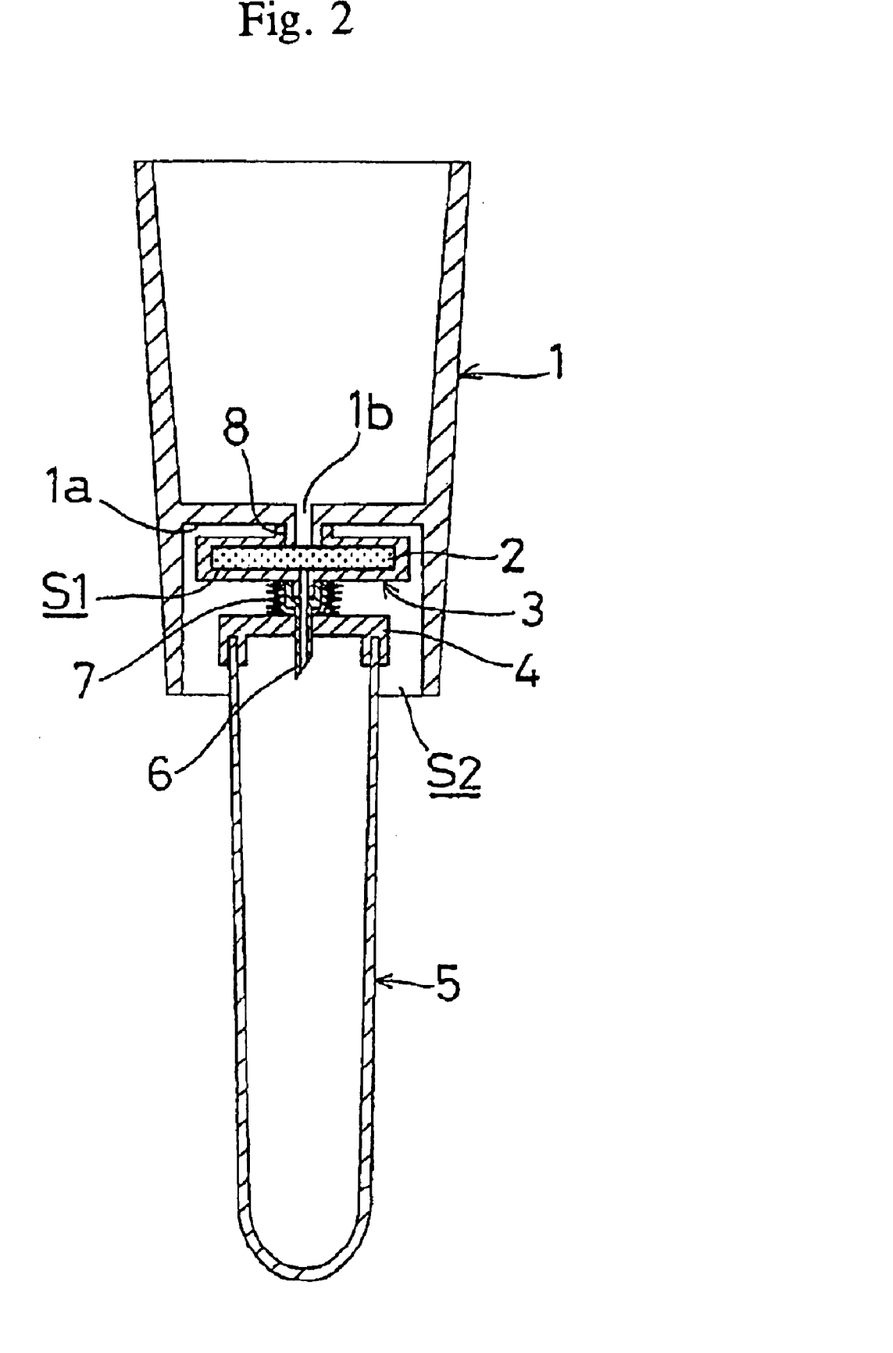
FIG. 2 is a sectional view of the device for sampling and storing a urine specimen according to the present invention in FIG. 1, which is in use.

With the device for sampling and storing a urine specimen as shown in FIG. 1, the method for sampling and storing a urine specimen is carried out, as follows. As shown in FIG. 2, the needle 6 attached at the top of the filter holder 3 pierces the bottom 1a of the sampling cup 1 of a sampled urine specimen through the rubber cap 7, and the other needle 6 attached the bottom of the filter holder 3 pierces the plug 4 of the decompressed and sealed recovery container 5 through the rubber cap 7 alike. Consequently, a urine specimen sampled in the sampling cup 1 flows into the recovery container 5 through the filter 2 by sucking pressure to be recovered.

In FIG. 3, the filter holder 3 has a space S1 for holding the filter 2 inside, a communicating hole 8 at its upper inlet side for a specimen and a needle 6 at its lower outlet side for a specimen. The communicating hole 8 is communicating with a bottom hole 1b of the sampling cup 1, and the needle 6 is communicating with the space S1 of the filter holder 3. A rubber cap 7 covers around the needle 6 so as to avoid a user's injury such as pricking his or her fingers with the needle the same as in FIG. 1. Additionally, a space S2, wherein the filter holder 3 can be held, is provided at the bottom of the sampling cup 1 to prevent the filter holder 3 from projecting over the bottom of the sampling cup 1.

Figure 4:
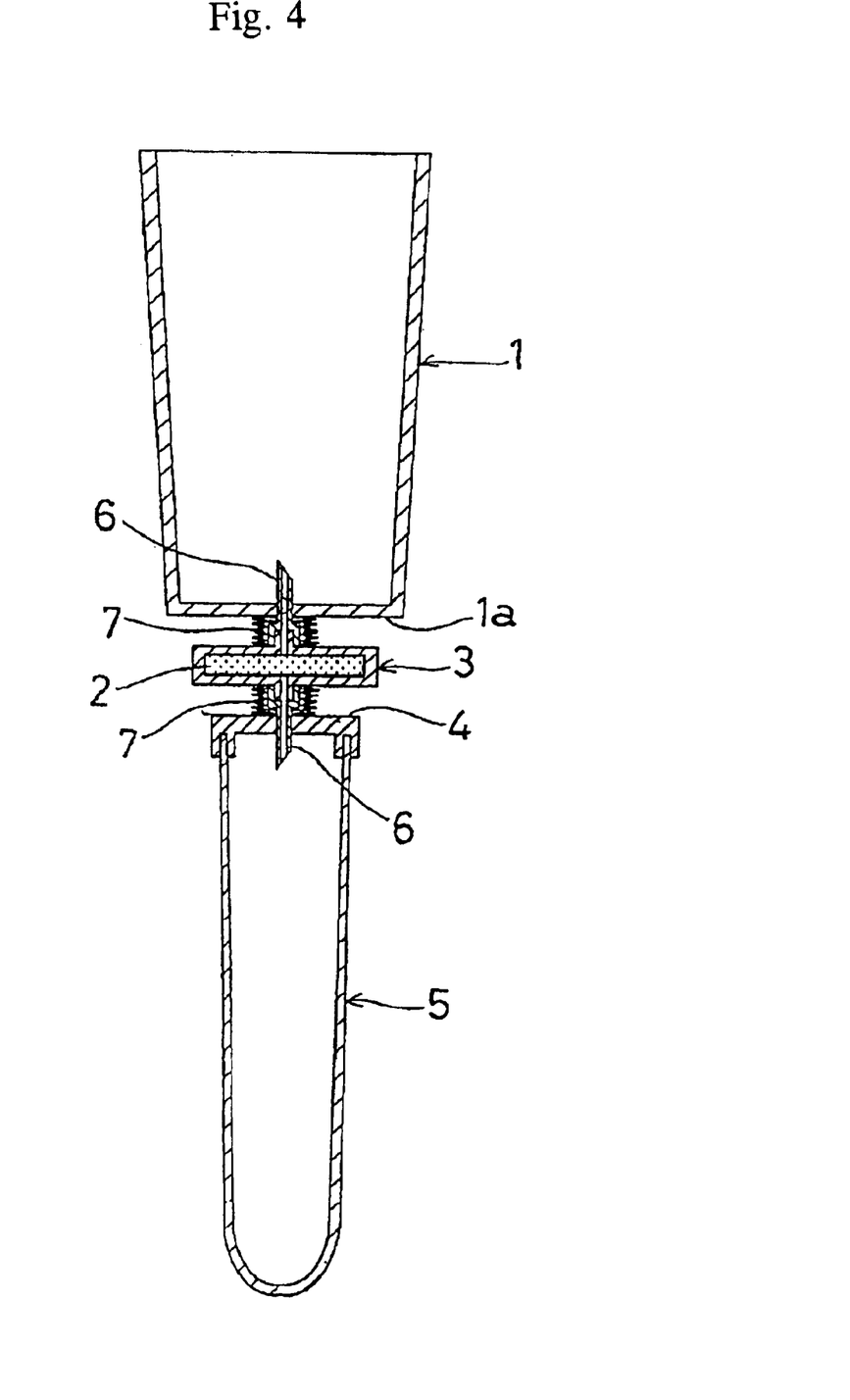
FIG. 4 is a sectional view of the device for sampling and storing a urine specimen according to the present invention in FIG. 3, which is in use.

Therefore, as shown in FIG. 4, in order to carry out the method for sampling and storing a urine specimen with the device for sampling and storing a urine specimen according to FIG. 3, the needle 6 attached at the bottom of the filter holder 3 pierces the plug 4 of the decompressed and sealed recovery container 5 through the rubber cap 7, and the urine specimen sampled in the sampling cup 1 consequently flows into the recovery container 5 through the filter 2 by sucking pressure to be recovered.

As long as the sampling cup 1 can be pierced by the needle 6 to recover a urine specimen without an excessive leak of the specimen, neither its shape nor materials is limited.

Figure 5:
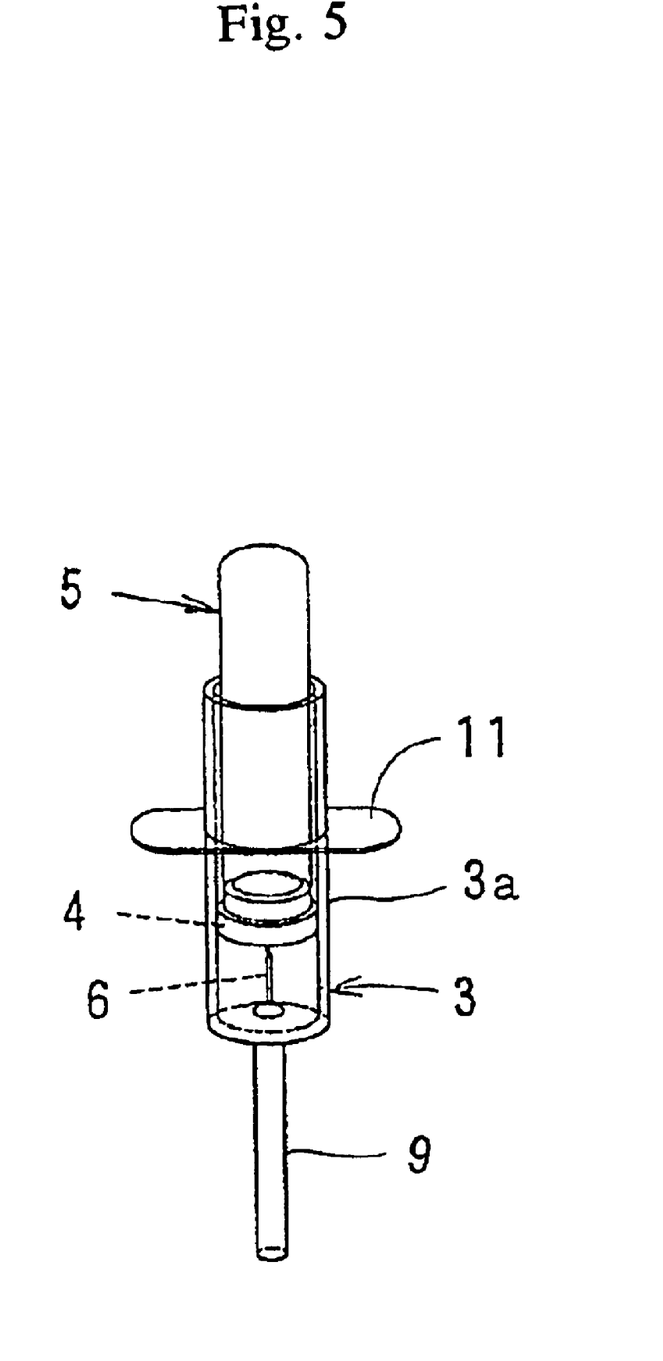
FIG. 5 is a perspective view of another embodiment of a device for sampling and storing a urine specimen according to the present invention.

Furthermore, another device for sampling and storing a urine specimen of the present invention, as shown in FIG. 5, includes a filter 2 for a urine specimen, a filter holder 3 holding the filter 2, a plug 4, and a recovery container 5 decompressed and sealed with the plug 4.

The filter holder 3 has a space S to hold the filter 2 inside, an outer cover 3a extending upward on its outlet side for a specimen, a needle 6 within the outer cover 3a, and a specimen suction tube 9 at its lower inlet side for a specimen. The needle 6 and the specimen suction tube 9 are communicating with the space S. In order to make the specimen suction tube 9 communicate with the space S, the specimen suction tube 9 is communicating with a communicating hole 10a of a cap 10 which seals the space S from below. A manipulation flange 11 is attached around the outer cover 3a.

The recovery container 5 is insertable into the outer cover 3a of the filter holder 3 with the plug 4 ahead.

Figure 6:
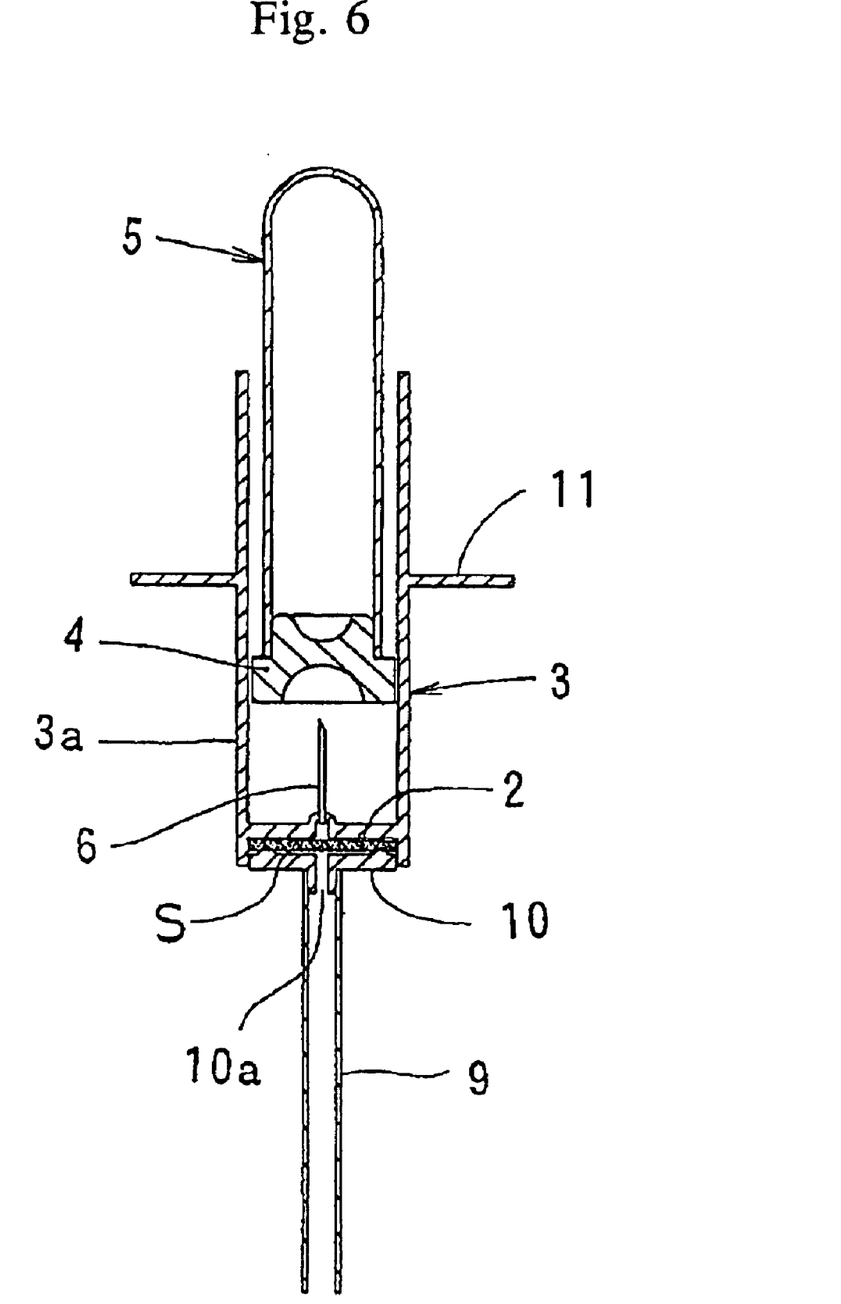
FIG. 6 is a sectional view of the device for sampling and storing a urine specimen according to the present invention in FIG. 5.
Figure 7:
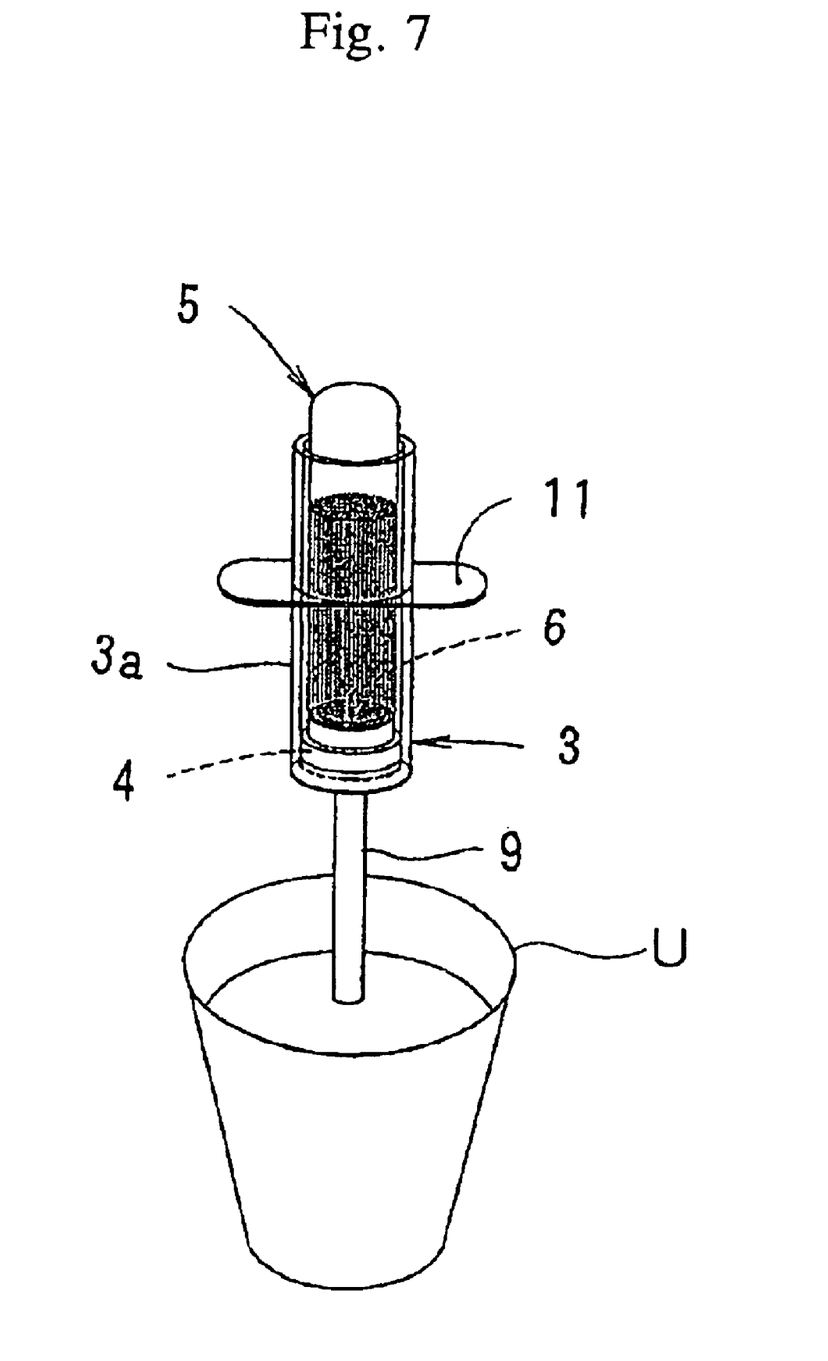
FIG. 7 is a perspective view of the device for sampling and storing a urine specimen according to the present invention in FIG. 5, which is in use.
Figure 8:
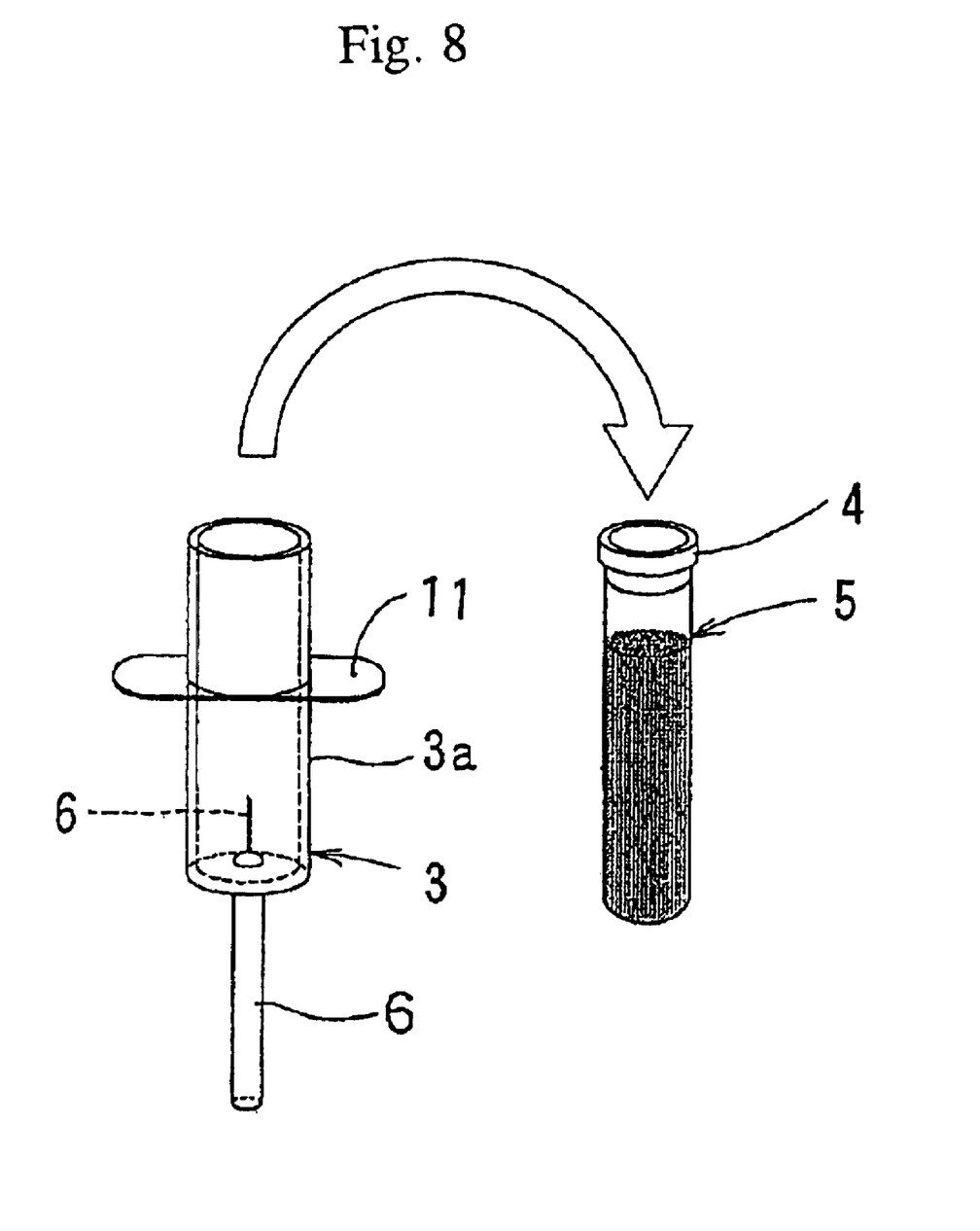
FIG. 8 is a perspective view of the device for sampling and storing a urine specimen according to the present invention in FIG. 5, which is in use.

As shown in FIGS. 5 and 6, in the above-mentioned device for sampling and storing a urine specimen according to the present invention, the recovery container 5 is put into the outer cover 3a of the filter holder 3 with the plug 4 ahead to in front of the needle 6. Then as shown in FIG. 7, the specimen suction tube 9 is put into the urine specimen sampled in a sampling container U or the like, and the recovery container 5 is inserted into the outer cover 3a of the filter holder 3 even deeper to make the needle pierce the plug 4. Consequently, the urine specimen sampled in the sampling container U or the like flows from the specimen suction tube 9 into the recovery container 5 through the filter 2 by sucking pressure. Furthermore, as shown in FIG. 8, the recovery container 5 is drawn out of the filter holder 3, and consequently, the needle 6, which has pierced the plug 4 is drawn therefrom. And the urine specimen is sampled and stored in the recovery container 5.

In the above-mentioned operation, the recovery container 5 can be easily inserted into the outer cover 3a of the filter 3 and also easily drawn therefrom because of the manipulation flange 11.

The specimen suction tube 9 can be made of glass or plastics, and it does not matter whether the specimen suction tube 9 is flexible or not. The inside diameter is not limited as long as it does not hinder a urine specimen from flowing into the decompressed and sealed recovery container 5 by sucking pressure.

In the above-mentioned embodiment, the filter 2 held within the filter holder 3 is favourably made of cellulose acetate, polysulfone, or polyether sulfone, which have low adsorptivity for constituents of urine such as protein, and the pore size is favourably 0.05 $\mu$m–0.2 $\mu$m in order to enable a urine specimen to be smoothly filtered but not germs.

The recovery container 5 has material and structure that shut out the air, and it is sealed with the plug 4 made of synthetic rubber or the like after being decompressed by being filled with inert gas such as nitrogen gas. The recovery container 5 needs to be decompressed enough to be able to recover an adequate amount of specimen. Although it depends on material, the pressure in the recovery container 5 is favourably 0.1 atm–0.5 atm because extreme decompression affects efficiency of keeping the pressure and durability of the container.

The size and sharp of the recovery container 5 are favourably like of a test tube or a bottle which can be put on a common device for a urine test, but not limited. In FIG. 5, they are not limitative as long as the recovery container 5 is insertable into the filter holder 3 with the plug 4 ahead. Furthermore, it is advisable that the recovery container 5 does not transmit light so that effect of light on a sampled urine specimen can be reduced.

As shown in FIG. 6, the plug 4 of the recovery container may be provided with a recess on an upper and/or a lower side thereof, and the recess provides a thinner portion on the plug. Therefore, the needle can easily pierce the plug at the thinner portion and can be readily drawn therefrom, and still the plug maintains durability against decompression.

Specific Examples of Operation of Invention

The present invention is concretely described, referring to the following specific examples.

With the device for sampling and storing a urine specimen of the present invention according to FIG. 3, the method for sampling and storing a urine specimen of the present invention was operated, and the constituents of the urine specimens were determined after 0–7 days.

First of all, the urine specimens A–E were taken into the sampling cups 1 respectively. Next, the needles 6 each attached at the bottom of the filter holders 3 were pierced the plugs 4 of the decompressed and sealed recovery containers 5. Then the urine specimens, which had been sampled in the sampling cups 1, flowed through filters 2 into the recovery containers 5 by sucking pressure. After that, the needles 6 which had been pieced the plug 4 were drawn therefrom, and the containers were kept at room temperature for 0–7 days, being sealed with the plugs 4. The filters 2 were made of cellulose acetate by Advantech Co., Ltd. Their pore sizes were 0.2 $\mu$m, and their diameters were 50 mm. The recovery containers 5 were brown plastic test tubes which were decompressed to 0.2 atm and were sealed with rubber plugs.

In contrast, as examples for comparison, the rest of the urine specimens A–E which had been collected in the above-mentioned sampling cups were recovered into brown plastic test tubes and let to stand at room temperature for 0–7 days.

The constituents of the specimens were determined by a urine test instrument (US-3100) made by Eiken Chemical Co., Ltd. shortly after starting storing, 2 days, 4 days and 7 days respectively. The results of the determination are shown in Tables 1–5.

TABLE 1

| | | Examples | | | | Comparative Examples | | | |
|---|---|---|---|---|---|---|---|---|---|
| | | shortly after starting storing | after 2 days | after 4 days | after 7 days | shortly after starting storing | after 2 days | after 4 days | after 7 days |
| Specimen A | colour | yellow | yellow | yellow | yellow | yellow | yellow | yellow | straw |
| | gravity | 1.008 | 1.010 | 1.010 | 1.012 | 1.012 | 1.008 | 1.009 | 1.007 |
| | pH | 6.0 | 6.0 | 6.0 | 6.0 | 6.0 | 6.5 | 7.0 | 7.5 |
| | sugar | — | — | — | — | — | — | — | — |
| | protein | — | — | — | — | — | — | — | — |
| | ketones | — | — | — | — | — | — | — | — |
| | bilirubin | — | — | — | — | — | — | — | — |
| | urobilinogen | ± | ± | ± | ± | ± | ± | ± | ± |
| | nitrite | — | — | — | — | — | — | — | 1+ |
| | glucose (mg/dl) | — | — | — | — | — | — | — | — |

TABLE 2

| | | Examples | | | | Comparative Examples | | | |
|---|---|---|---|---|---|---|---|---|---|
| | | shortly after starting storing | after 2 days | after 4 days | after 7 days | shortly after starting storing | after 2 days | after 4 days | after 7 days |
| Specimen B | colour | yellow | yellow | yellow | yellow | yellow | straw | straw | straw |
| | gravity | 1.038 | 1.036 | 1.039 | 1.039 | 1.039 | 1.036 | 1.038 | 1.035 |
| | pH | 7.0 | 7.0 | 7.0 | 7.0 | 7.0 | 7.5 | 8.0 | 8.5 |
| | sugar | 4+ | 4+ | 4+ | 4+ | 4+ | 4+ | 4+ | 4+ |
| | protein | 1+ | 1+ | 1+ | 1+ | 1+ | 1+ | — | — |
| | ketones | 1+ | 1+ | 1+ | 1+ | 1+ | — | — | — |
| | bilirubin | — | — | — | — | — | — | — | — |
| | urobilinogen | ± | ± | ± | ± | ± | ± | ± | ± |
| | nitrite | — | — | — | — | — | — | 1+ | 2+ |
| | glucose (mg/dl) | 6,200 | 6,188 | 6,219 | 6,182 | 6,253 | 6,185 | 6,077 | 5,882 |

TABLE 3

| | | Examples | | | | Comparative Examples | | | |
|---|---|---|---|---|---|---|---|---|---|
| | | shortly after starting storing | after 2 days | after 4 days | after 7 days | shortly after starting storing | after 2 days | after 4 days | after 7 days |
| Specimen C | colour | straw | straw | straw | straw | straw | straw | straw | amber |
| | gravity | 1.022 | 1.023 | 1.023 | 1.021 | 1.024 | 1.023 | 1.025 | 1.023 |
| | pH | 6.0 | 6.0 | 6.0 | 6.0 | 6.0 | 6.0 | 7.0 | 8.0 |
| | sugar | 2+ | 2+ | 2+ | 2+ | 2+ | 2+ | 1+ | 1+ |

TABLE 3-continued

|  |  | Examples | | | | Comparative Examples | | | |
|---|---|---|---|---|---|---|---|---|---|
|  |  | shortly after starting storing | after 2 days | after 4 days | after 7 days | shortly after starting storing | after 2 days | after 4 days | after 7 days |
|  | protein | — | — | — | — | — | — | — | — |
|  | ketones | — | — | — | — | — | — | — | — |
|  | biliruhin | — | — | — | — | — | — | — | — |
|  | urobilinogen | ± | ± | ± | ± | ± | ± | ± | ± |
|  | nitrite | — | — | — | — | — | 1+ | 1+ | 2+ |
|  | glucose (mg/dl) | 116 | 112 | 118 | 120 | 117 | 114 | 75 | 48 |

TABLE 4

|  |  | Examples | | | | Comparative Examples | | | |
|---|---|---|---|---|---|---|---|---|---|
|  |  | shortly after starting storing | after 2 days | after 4 days | after 7 days | shortly after starting storing | after 2 days | after 4 days | after 7 days |
| Specimen D | colour | straw | straw | straw | straw | straw | straw | amber | amber |
|  | gravity | 1.031 | 1.033 | 1.028 | 1.030 | 1.030 | 1.028 | 1.031 | 1.030 |
|  | pH | 7.5 | 7.5 | 7.5 | 7.5 | 7.5 | 8.0 | 8.5 | 8.5 |
|  | sugar | 3+ | 3+ | 3+ | 3+ | 3+ | 3+ | 3+ | 2+ |
|  | protein | 2+ | 2+ | 2+ | 2+ | 2+ | 2+ | 1+ | 1+ |
|  | ketones | — | — | — | — | — | — | — | — |
|  | bilirubin | — | — | — | — | — | — | — | — |
|  | urobilinogen | ± | ± | ± | ± | ± | ± | ± | ± |
|  | nitrite | 1+ | 1+ | 1+ | 1+ | 1+ | 2+ | 2+ | 2+ |
|  | glucose (mg/dl) | 558 | 567 | 535 | 563 | 563 | 446 | 283 | 158 |

TABLE 5

|  |  | Examples | | | | Comparative Examples | | | |
|---|---|---|---|---|---|---|---|---|---|
|  |  | shortly after starting storing | after 2 days | after 4 days | after 7 days | shortly after starting storing | after 2 days | after 4 days | after 7 days |
| Specimen E | colour | yellow | yellow | yellow | yellow | yellow | yellow | straw | straw |
|  | gravity | 1.018 | 1.015 | 1.014 | 1.017 | 1.015 | 1.018 | 1.016 | 1.015 |
|  | pH | 6.5 | 6.5 | 6.5 | 6.5 | 6.5 | 7.0 | 7.0 | 7.5 |
|  | sugar | 1+ | 1+ | 1+ | 1+ | 1+ | — | — | — |
|  | protein | 1+ | 1+ | 1+ | 1+ | 1+ | 1+ | — | — |
|  | ketones | 2+ | 2+ | 2+ | 2+ | 2+ | 1+ | — | — |
|  | bilirubin | 1+ | 1+ | 1+ | 1+ | 1+ | — | — | — |
|  | urobilinogen | 1+ | 1+ | 1+ | 1+ | 1+ | ± | ± | ± |
|  | nitrite | — | — | — | — | — | 1+ | 1+ | 2+ |
|  | glucose (mg/dl) | 38 | 47 | 42 | 44 | 48 | 25 | — | — |

As the results shown in Tables 1–5, in the comparative examples, there were big fluctuations in some testing items such as colour, gravity, pH, sugar, protein and nitrite during 1–7 days, but in the examples, no fluctuation was found in the above items during 1–7 days.

Furthermore, with the device for sampling and storing a urine specimen of the present invention according to FIG. 5, urine specimens were sampled and stored, and their constituents were determined shortly after starting storing and after 7 days.

First of all, the urine specimens F–J were taken into sampling containers U or the like. Next, the specimen suction tubes 9 of the filter holders 3 were respectively put into the urine specimens F–J while the recovery containers 5 were inserted into the outer covers 3a with the plugs 4 ahead to in front of the needles 6. Then the recovery containers 5 were inserted into the outer covers 3a of the filter holders 3 even deeper to make the needles 6 pierce the plugs 4. Consequently, the urine specimens F–J respectively flowed from the specimen suction tubes 9 through the filters 2 into the recovery containers 5 by sucking pressure to be recovered. After that, the recovery containers 5 were drawn out of the filter holders 3, and consequently the needles 6 which had been pierced the plugs 4 were drawn therefrom, and the containers were kept at room temperature for 0–7 days being sealed with the plugs 4. The filters 2 were made of cellulose acetate by Advantech Co., Ltd. Their pore sizes were 0.2 μm, and their diameters were 50 mm. The recovery containers 5 were brown plastic test tubes which were decompressed to 0.2 atm and sealed with rubber plugs.

In contrast, as examples for comparison, the rest of the urine specimens F–J were collected in brown plastic test tubes and let to stand at room temperature for 7 days.

The constituents of the specimens were determined by a urine test instrument (US-3100) made by Eiken Chemical Co., Ltd. shortly after starting storing and after 7 days respectively. The results of the determination are shown in Table 6.

TABLE 6

| | | Examples | | | Comparative Examples | | |
|---|---|---|---|---|---|---|---|
| | | pH | sugar | protein | pH | sugar | protein |
| Specimen A | shortly after starting storing | 6.0 | — | — | 6.0 | — | — |
| | after 7 days | 6.0 | — | — | 7.5 | — | — |
| Specimen B | shortly after starting storing | 7.0 | 6,200 | 1+ | 7.0 | 6,253 | 1+ |
| | after 7 days | 7.0 | 6,182 | 1+ | 8.5 | 5,822 | — |
| Specimen C | shortly after starting storing | 6.0 | 116 | — | 6.0 | 117 | — |
| | after 7 days | 6.0 | 120 | — | 8.0 | 48 | — |
| Specimen D | shortly after starting storing | 7.5 | 558 | 2+ | 7.5 | 563 | 2+ |
| | after 7 days | 7.5 | 563 | 2+ | 8.5 | 158 | 1+ |

Since the present invention is composed as mentioned above, even if urine specimens are kept at room temperature for several days, constituents of urine specimens will not be changed, and accurate determination can be obtained. Also, in a group examination, urine specimens can be easily transported and tested without refrigeration or other treatment.

Furthermore, the device for sampling and storing a urine specimen of the present invention has a simple structure and can be easily used, and additionally a sampler does not need to touch a needle directly. Therefore, the device allows safe and easy sampling and testing in a region without enough equipment.

What is claimed is:

1. A method for sampling and storing a urine specimen comprising:
    filtering a sampled urine specimen to remove germs therefrom through a filter (2) which has a pore size of 0.05 μm–0.2 μm;
    decompressing and sealing a recovery container; and
    recovering the sampled urine specimen into the recovery container using sucking pressure therein.
2. A method for sampling and storing a urine specimen according to claim 1, in which the recovery container (5) does not transmit light.
3. A method for sampling and storing a urine specimen according to claim 2, wherein pressure in the recovery container is 0.1 atm–0.5 atm.
4. A method for sampling and storing a urine specimen according to claim 3, wherein the recovery container is decompressed and sealed after filled with inert gas.
5. A method for sampling and storing a urine specimen according to claim 2, wherein the recovery container is decompressed and sealed after being filled with inert gas.
6. A method for sampling and storing a urine specimen according to claim 1, in which pressure in the recovery container (5) is 0.1 atm–0.5 atm.
7. A method for sampling and storing a urine specimen according to claim 1, in which the recovery container (5) is decompressed and sealed after being filled with inert gas.
8. A method for sampling and storing a urine specimen according to claim 7, wherein pressure in the recovery container is 0.1 atm–0.5 atm.
9. A device for sampling and storing a urine specimen comprising:
    a filter (2) for removing germs from a sampled urine specimen, the filter (2) having a pore size of 0.05 μm–0.2 μm;
    a filter holder (3) which has a space S for receiving the filter (2);
    a plug (4);
    a recovery container (5) decompressed and sealed with the plug (4); and
    wherein the filter holder (3) is provided with the space (S) for holding the filter (2), an outer cover (3a) extending upward on its outlet side for a specimen, a tube (6) with a sharp tip communicating with the space (S) within the outer cover (3a), and a specimen suction tube (9) communicating with the space (S) on its inlet side for the specimen, and the recovery container (5) is insertable into the outer cover (3a) of the filter holder (3) with the plug (4) ahead.
10. A device for sampling and storing a urine specimen according to claim 9, in which the recovery container (5) does not transmit light.
11. A device for sampling and storing a urine specimen according to claim 9, in which pressure in the recovery container (5) is 0.1 atm–0.5 atm.
12. A device for sampling and storing a urine specimen according to claim 9, in which the recovery container (5) is decompressed and sealed after being filled with inert gas.

* * * * *